(12) United States Patent
Berghmans (10) Patent No.: US 8,259,298 B2
(45) Date of Patent: Sep. 4, 2012

(54) SORTING DEVICE WITH A BROAD SPECTRUM LIGHT SOURCE AND ACCORDING METHOD (75) Inventor: Paul Berghmans, Heverlee (BE)

(73) Assignee: Belgian Electronic Sorting Technology N.V., Heverlee (BE)

(*) Notice: Subject to any disclaimer, the term of this patent is extended or adjusted under 35 U.S.C. 154(b) by 63 days.

(21) Appl. No.: 12/676,210

(22) PCT Filed: Sep. 3, 2008

(86) PCT No.: PCT/BE2008/000070
§ 371 (c)(1),
(2), (4) Date: Mar. 3, 2010

(87) PCT Pub. No.: WO2009/030004
PCT Pub. Date: Mar. 12, 2009

(65) Prior Publication Data
US 2010/0198397 A1    Aug. 5, 2010

(30) Foreign Application Priority Data
Sep. 3, 2007  (EP) .................................. 07447051

(51) Int. Cl.
G01N 21/00  (2006.01)
(52) U.S. Cl. .................................. 356/338; 356/237.1
(58) Field of Classification Search ........... 356/336–342
See application file for complete search history.

(56) References Cited

U.S. PATENT DOCUMENTS

| 5,923,683 | A   | 7/1999  | Morioka et al. |       |
|-----------|-----|---------|----------------|-------|
| 6,864,970 | B1  | 3/2005  | Ruymen et al.  |       |
| 7,130,512 | B2* | 10/2006 | Kuksenkov et al. | 385/122 |
| 7,768,643 | B1* | 8/2010  | Janssens et al. | 356/369 |
| 7,816,616 | B2* | 10/2010 | Kenny et al.   | 209/576 |

FOREIGN PATENT DOCUMENTS

EP    0729057 A2    8/1996

* cited by examiner

Primary Examiner — Michael P Stafira
(74) Attorney, Agent, or Firm — Browdy and Neimark, PLLC (57) ABSTRACT The invention relates to a system comprising a broadband optical light source and a sorting device and more specifically to laser sorting devices. The object of the present invention is to provide a system comprising a sorting device with a light-source offering all wavelengths for the sorting process. This is solved by using an all fiber supercontinuum light source.

18 Claims, 6 Drawing Sheets

SORTING DEVICE WITH A BROAD SPECTRUM LIGHT SOURCE AND ACCORDING METHOD

The invention concerns a method and a sorting apparatus for detecting irregularities in a product, in which at least one light beam is directed towards this product by means of a moving mirror, whereby the product moves in a particular direction through a detection zone, so that said light beam, which preferably moves transversely across the path of the product, is at least partially scattered and/or reflected by said product. The scattered and/or reflected light is detected by at least one detector in order to characterize and to sort the product.

Such sorting apparatuses are, for example, disclosed in the prior art documents U.S. Pat. Nos. 6,864,970, 4,723,659, EP 0 952 895 and EP 1 012 582.

In laser sorting devices, the products are sorted according to different sorting principles including a set of selection parameters, e.g. absorption, fluorescence, scattering or state of polarization. Most of the sorting principles are based on a set of specific discrete wavelengths of laser sources.

However, many very specific laser wavelengths, which are relevant for the sorting process, are commercially not available or the laser sources are voluminous and/or expensive and/or not reliable. Moreover, another problem is the combination of several lasers in one sorting system, which both increases the complexity of the optical system and requires a large stock of spare laser light sources.

When several laser sources are used in a sorting apparatus, the beams of these laser sources are combined into one single beam. However, the shape of the cross-section of the beam of the laser sources in most cases differ from each other. Further, many laser beams have a elliptical cross-section such that it is extremely difficult to combine these laser beams into one single beam with a uniform and homogenous cross-section. For the accuracy of the sorting process, it is however important that the cross-section of the light beam that impinges upon the products to be sorted has a cross-section that is uniform and presents a homogenous distribution of light frequencies.

The impingement of a laser beam onto a product having an irregular surface gives rise to interference phenomena. This is particularly the case when the size of an unevenness in the surface of a product is of the same size as the wavelength of the impinging laser beam. The resulting signal generated by the reflected light beam at the detectors of the sorting device has thus a limited accuracy.

Further, existing laser sorting apparatuses are provided with a fixed set of laser sources with light frequencies that are selected in function of the type of products to be sorted. A specific laser sorting apparatus is thus only usable for sorting a certain type of products and for determining a certain type of defects or foreign objects. Each sorting process requires its own light frequencies. It is very cumbersome to adapt such laser sorting apparatuses in order to allow sorting of other types of products since other light frequencies may be required for sorting such other products.

Sorting apparatuses can also be provided with whitelight broadband sources, for example high intensity discharge lamps (HID lamps) such as Xenon bulbs. The problem with these broadband sources is the generated light has a low spatial coherence and brightness and a very low coupling efficiency towards optical fibers. Further, the use of HID lamps is subject to relatively warm-up times and restrike times.

Sorting apparatuses with broadband bulbs as light source are not giving satisfying results since the light sources have a low power and a low resolution.

Laser sorting apparatuses further have the disadvantage that laser sources for only a restricted number of specific wavelengths are available or that laser sources for certain wavelengths are too bulky or expensive to be used in a sorting apparatus. Another disadvantage of existing laser sorting apparatuses is the fact that the different types of lasers require separate and special electronics and power supplies etc. A further disadvantage is the need of a large amount of special optics, such as dichroic mirrors to combine the multiple laser beams into one beam and the possibility of misalignment of the laser beams during operation.

Laser sorting apparatus that use optical fibers for guiding the laser beams have multi mode problems in polychromatic sorting applications. A further disadvantage is the limited bandwidth of conventional single mode fibers (operation window).

The invention generally relates to the field of sorting apparatuses and in particular to the optical scanning systems in sorting devices and more specifically to broadband sorting devices. In such sorting apparatuses, a light beam is directed towards products to be sorted and impinges upon these products. The reflected light is detected and on basis of this detected light the products are sorted or characterised.

With the term broadband sorting is in this context meant a sorting process using a collection of wavelengths distributed over a wide spectral range, such as the ultraviolet and the visible and such as the visible and near-infrared and such as the ultraviolet, the visible and the infrared.

Moreover the invention generally relates to the use of photonic crystal fibers in combination with sorting devices, such as a food sorting machine, such as optical scanning systems, such as for scanning products such as food and plastics, such as for elimination of strange objects and such as for the sorting on quality, such as oil and water content.

The invention generally relates to white light sources and more particularly to the use of white light sources in sorting devices, for example broadband light sources.

The invention relates specifically to a sorting device with an optical waveguide broadband supercontinuum light source, such as a supercontinuum generated in a photonic crystal fiber.

The invention furthermore relates to a sorting device with an optical waveguide system, said system comprising an optical fiber and specifically comprising of an endlessly single mode fiber.

The invention furthermore relates to the use of an endlessly single mode optical fiber to guide light into a focusing system of a sorting apparatus.

The invention furthermore relates to the use of said waveguide based supercontinuum light source and said endlessly single mode waveguide system in a sorting apparatus.

In the following a short description is given of this sorting apparatus, followed by the prior art related to the optical system as related to the invention.

The optical laser scanning system of the sorting device, according to the invention, briefly, has:
1) an optical sending side comprising a supercontinuum radiation source,
2) a scanning element, such as a polygon mirror, and
3) an optical receiving side comprising detection means.

The sending side is provided with a light source to illuminate the products to be sorted on a small area or spot via a focusing system. It is common that multiple wavelengths are required for the sorting process to increase the sorting parameters and articles to be sorted.

According to the prior art, multi-line laser systems are used for this purpose, or lasers with different wavelengths are combined into a single beam by the use of dichroic mirrors. For the sorting process it is important that the light beams of these multiple sources have a similar spot size and coincide or superimpose in the same spot of the sorting article, which increases the sorting efficiency and accuracy.

For example in the prior art patent applications EP 0 620 051 A1 (equivalent to U.S. Pat. No. 5,729,473) and EP 0 736 339 A1, the sorting of products, such as fruits an vegetables, is performed by the illumination with a polychromatic beam composed of a discrete number of pre-selected wavelengths combined with a monochromatic beam, for example an infrared wavelength, superimposed in a single spot. The disadvantage of these applications is the dependence on the availability of the discrete laser lines and, as already mentioned, the cumbersome superposition of the multiple light beams.

It is known from the document U.S. Pat. No. 5,729,473 that the light beam from a multi-line laser is combined into one optical fiber. The output of the multi-line laser, containing the distinct colors red, green and blue is first combined in an optical fiber and afterwards combined in free space with an infrared source. Therefore the method as disclosed in the mentioned patent is not particularly suitable for broadband sorting applications. The disadvantage of the use of said method of optical waveguides for broadband applications is the multimode character of wavelengths below the cut-off wavelength of the optical waveguide and high losses above an upper wavelength, i.e. guidance in the fundamental mode is only possible in a narrow band operation window. For the purpose of sorting, multimode guidance of the light beams results in an irregular and larger spot size and therefore in a reduced resolution, efficiency and accuracy. This is particularly the case for wavelengths that are spectrally widely separated, as is the case in broadband sorting applications. In broadband sorting applications, the wavelengths of the multiple light sources are typically in the visible and the near infrared range such as 488 nm, 830 nm and 980 nm, but are not restricted only to these wavelengths and can also include the UV wavelengths between 350 nm and 488 nm and infrared wavelengths of 1100 nm up to 3 µm. Especially the wavelength range between 1100 and 1600 nm is of importance because of the water and oil absorption characteristics of the sorting articles. And the wavelengths between 1000 and 3000 nm are of importance for the sorting of plastic materials.

A disadvantage of the current broadband sorting technology is that many of the commercially available laser sources, or even the laser technology in general, do not accommodate to the very specific wavelengths as required for the broadband sorting process. Yet another disadvantage of current multi-line laser sources is the limited total number of wavelengths included. Therefore in many situations still the laser sources need to be coupled into one single beam by coupling optics with the consequent disadvantages as described above.

As an alternative to the use of laser sources in sorting devices, use can be made of broadband light sources, such as halogen bulbs. It is known from for example the document U.S. Pat. No. 5,333,739 or RU 2 012 430 that traditional broadband or white light sources are used in sorting machines. Until now, these light sources used in these systems could for example be high intensity discharge lamps (HID), such as Xenon or tungsten-halogen bulbs, or light emitting diodes (LEDs) and especially super luminescence LEDs (SLEDs). These sources however are limited either by brightness and/or spectral width and spectral shape. Xenon lamps for example have a low spatial coherence which results in a low illumination efficiency.

Additional to these light sources, it is known from the document U.S. Pat. No. 5,333,739 that in a system for fluid inspection, light of a quartz halogen light bulb is focused into a quartz-glass optical fiber cable. The efficiency of coupling light of the HID bulbs, or bulbs in general, into an optical fiber is generally very low.

The aim of the present invention is to remedy the above-mentioned disadvantages and problems.

To this aim, the sorting device, according to the invention, comprises a supercontinuum radiation source for characterizing products in a stream of products. This supercontinuum radiation source generates a light beam having a broadband spectrum, in particular a coherent light beam, that impinges upon said products in a detection zone such that light is scattered and/or reflected by the products, whereby detection means are provided for detecting said scattered and/or reflected light, said detection means cooperating with a processing unit for characterizing the products.

The phenomenon of supercontinuum is best described as the spectral broadening of light of a seed laser by nonlinear interaction with a medium. Said seed laser source can both be pulsed or continuous wave. Said supercontinuum can be generated in a variety of materials, depending among others on the nonlinearity and dispersion of the material, as well as both the wavelength and the intensity of the light propagating through the material. It is well known in the field of fiber optics that supercontinuum can be generated in optical waveguides and more specific in optical fibers. Optical fibers have the advantage of a high modefield confinement to the core region, which increases the localized intensity and the nonlinear interactions.

Very recently, supercontinuum generation (SCG) was for the first time established in photonic crystal fibers (PCF) (J. K. Ranka, R. S. Windeler, and A. J. Stentz, "Visible continuum generation in air-silica microstructure fibers with anomalous dispersion at 800 nm," Opt. Lett. 25, 25-27 (2000)). The advantage of the use of these optical fibers is the control over the fiber parameters defining the modefield, the dispersion and nonlinear processes, which are the key design parameters of the medium to define the properties of the supercontinuum. Nonlinearities in the photonic crystal fibers (PCF) can be enhanced by decreasing the modefield diameter and confining the light to the solid core region, increasing the intensity and therefore nonlinear interaction with the core material. The PCF is especially advantageous to obtain a high degree of mode confinement to the core region due to the high index contrast between the core region and the air-cladding. Also highly nonlinear fibers (HNLF) can be used for the generation of supercontinuum. These HNLF typically exhibit a small effective area and low and flat dispersion profile ("Pulsed and continuous-wave supercontinuum generation in highly nonlinear, dispersion-shifted fibers", J. W. Nicholson, Appl. Phys. B77, 2003).

Though compared with the PCF, the classical design of an optical fiber, including the HNLF, shows a significant lower freedom of design of the dispersion profile. The dispersion profile is of high importance, and in particular the wavelength at which the dispersion is zero. Ultra broadband supercontinuum can be generated by pumping the PCF with a high intensity pulsed laser having a wavelength in the anomalous region of dispersion and close to the zero dispersion wavelength (Genty, 'Route to supercontinuum', Proceedings CLEO 2002). Another advantage of the freedom of design of the dispersion profile in PCF is that the profile can be matched to the wavelength of low-cost pump lasers (S. G. Leon-Saval, T. A. Birks, W. J. Wadsworth and P. St. J. Russell, M. W. Mason, 'Supercontinuum generation in submicron fibre Waveguides', Optics Express, Vol. 12, No. 13, Page 2864)

Yet another advantage is that the spectral width can be designed such that the spectrum spans from the UV up to the mid-infrared ("Generation of High-Power Femtosecond Pulse and Octave-Spanning Ultrabroad Supercontinuum Using All-Fiber System", J. Takayanagi, N. Nishizawa, H. Nagai, M. Yoshida, T. Goto, IEEE PHOTONICS TECHNOLOGY LETTERS, VOL. 17, NO. 1, 2005) or such that enhancement of the intensity is achieved in only a specific wavelength range ("Supercontinuum generation in a fiber grating", P. S. Westbrook, J. W. Nicholson, K. S. Feder, Y. Li, T. Brown, APPLIED PHYSICS LETTERS VOL. 85, NO. 20, 2004). Recently supercontinuum has been shown in non-silica glasses such as chalcogenide, opening up for wavelengths beyond 2000 nm where the background attenuation of silica strongly increases (L. B. Shaw et al. Adv. Solid State Photonics Tech. Digest, paper TuC5, Austria (Feb. 6-9, 2005), Supercontinuum sources are now commercially available with spectral ranges typically ranging from the UV into the near infrared, featuring a high spectral density and high spatial coherence length. One of the first commercially available whitelight source based on supercontinuum generation in PCF was for example from the company Koheras A/S in Denmark in 2004.

The freedom of design of the photonic crystal fiber also opened up for the possibility of true single mode guidance over the total transmission window of silica. This fiber, the endlessly single mode fiber, is known from the patent application WO 00/37974. It is known in the field of photonic crystal fibers (PCF) (Birks, T. A., Knight, J. C., and Russel, P. St. J.: "Endlessly single-mode photonic crystal fiber", Opt. Lett., 1997, 22, p. 961) that using a specific type of waveguide single mode guidance can be achieved over a very broad spectral range. Conventional single mode optical waveguides have an operating window limited by the lower wavelength cut-off and an upper wavelength above which losses dominate the guidance. Below the cut/off wavelength the guidance will be in, besides the fundamental mode, higher order modes and is therefore multimode, resulting in a larger and more irregular spot. This problem is especially severe in those circumstances where wavelengths are spectrally widely separated from each other, e.g. a wavelength of 365 nm and 980 nm, which are the sorting wavelengths for aflatoxines and water absorption respectively.

The ESM waveguides are designed typically with a solid core surrounded by a cladding of a carefully designed lattice of air holes. The cladding raises the index contrast with the core, therefore confining the light in the core. Low wavelengths will be mainly confined to the core region only, with almost no penetration of the tails of the field, or evanescent field, into the cladding. This situation is comparable to the classical single mode fiber without an air cladding. Increasing the wavelength will also increase the tails of the optical field or evanescent field in the cladding. The more the field penetrates into the cladding the higher will be the index contrast with the core, therefore the cladding effective index strongly depends on the wavelength, and it can be shown mathematically and experimentally that therefore the light remains single mode.

The supercontinuum light source is readily used in a variety of applications. In the following some of the current developments are summarized.

The use of supercontinuum in microscopy is known in for example the prior art "Chromatic confocal microscopy using supercontinuum light", K. Shi, P. Li, S. Yin, Z. Liu, Optics Express, Vol. 12, No. 10, 2004 and "Confocal laser scanning fluorescence microscopy with a visible continuum source", G. McConnell, Optics Express, Vol. 12, No. 13, 2004. The articles describe the spectral components of the supercontinuum being focused, directly from the output of the supercontinuum source, at different depth levels using the chromatic aberration of the focusing system, which enables the three dimensional mapping of a structure.

Preferably, the sorting device, according to the invention, has a polarized broadband high intensity light source in the fundamental mode of an endlessly single mode fiber, i.e. the nonlinear fiber and endlessly single mode fiber are an all-in-one combination.

Possibly, in case of single mode issues, this can be a combination of NLF and ESMF Also the combination of the current multiple lasers coupled into a ESMF is possible.

Another advantage of using a ESMF is the diffraction limited beam width over the whole spectrum.

It is also important to note that the continuum of available wavelengths in a light beam generated by a supercontinuum light source makes it possible to sort products and/or to apply techniques (e.g. for sorting plastics or for sorting products on their oil/water content) that was not possible with the prior art sorting apparatuses.

In the present invention a supercontinuum light source is used in a sorting device.

In an advantageous embodiment of the sorting device, according to the invention, an all-optical waveguide based supercontinuum light source is used.

This optical waveguide is a preferably a photonic crystal fiber.

In a particular interesting embodiment of the invention, this photonic crystal fiber is an endlessly single mode fiber.

The light of said supercontinuum source is preferably guided by means of an endlessly single mode fiber (ESMF) into the sorting device.

According to the invention, it is possible to guide the light of at least two laser sources by means of an ESMF into the sorting device.

The light beam emerging from an endlessly single mode fiber is focused into a small single spot onto the products to be sorted.

The advantage of the use of a supercontinuum source in a sorting device is the availability of all wavelengths in an extremely broad spectral range. The broad spectrum of the supercontinuum source offers a high degree of freedom to choose any specific wavelength or any combination of specific wavelengths. This makes it possible to choose wavelengths, which otherwise would be difficult to achieve with other light sources such as laser sources such as for example semi-conductor or bulk laser sources. The possibility to choose a combination of specific wavelengths in the sorting system has the advantage that the number of sorting selection parameters within different fields of sorting principles, such as color or fluorescence sorting, can be increased. An increase in the number of sorting selection parameters results in not only a more efficient and accurate sorting system, but also an increase of the types of articles to be sorted. The use of supercontinuum in the sorting device for example can open up for the sorting of products based on their oil and water contents, which is of particular interest for sorting products such as nuts and olives.

Another advantage of the use of the supercontinuum source compared with lasers and/or multi-line lasers in the sorting device is the flexibility to choose the total power incident on either the product or the detectors that are receiving light that is reflected by the products to be sorted. This can be regulated by providing bandwidth or band-pass filters, which are placed either directly after the light source or in front of the detectors. The bandwidth is directly proportional with the transmitted power in the selected wavelength range of the band-pass, something, which is not applicable for laser sources. In this way a low power supercontinuum source could be combined with high bandwidth band-pass filters in order to obtain a high power beam that is impinging upon the products. A low power supercontinuum source has advantages with respect to the reliability and the usability. The usability of laser driven machines is restricted by the laser class and defines the requirements for the design of the sorting machine with respect to the safety of the user. A lower power is also expected to increase the level of reliability due to a lower thermal load on the optical components.

The use of the supercontinuum light source in a sorting device has the advantage of providing the typical characteristics of laser light, i.e. the ability of a high degree of collimation, high intensity, divided over a very broad spectrum with a high spectral density from which the sorting wavelengths can be chosen. It is yet another advantage that only a single light source is needed, which is advantageous both economically, i.e. a smaller stock of spare light sources is required, and from the perspective of reduced complexity of the system design.

Another advantage is the control over the state of polarization of the supercontinuum light source generated in a photonic crystal fiber. Polarized light can be of crucial importance for the sorting of, for example, wet products or highly reflective products. Either the generated supercontinuum can be non-polarized, i.e. the state of polarization is elliptical at the output of the source and can be subsequently polarized by broadband polarization beam-splitters, such as Glan-Thompsen or Glan-Taylor polarizers.

More advantageously the supercontinuum can be generated in one of the polarization states of a polarization maintaining photonic crystal fiber.

Yet another advantage is that the supercontinuum is generated in the PCF and therefore almost 100% of the generated light can be guided into the sorting system for the purpose of sorting, taking into account negligible losses in the optical guiding system or coupling losses with a waveguide system such as an optical fiber such as the ESMF. In comparison with a Xenon lamp, only a fraction of the total intensity would be able to be coupled into for example an optical fiber, due to significant coupling losses to the optical fiber.

In comparison with other broadband light sources, such as for example HID (high intensity density) bulbs, the supercontinuum source has the advantage of a very high spectral density and intensity, which is about three orders of magnitude higher than in case of a conventional white light source such as the HID bulbs. Another advantage is that the spectrum can span over more than two octaves (D. A. Akimov et all, "Spectral superbroadening of subnanojoule Cr: forsterite femtosecond laser pulses in a tapered fiber," J. Catal. 74, 460-463 (2001).). This is of particular relevance for the use in the wavelengths ranges above 1100 nm and particularly between 2000 and 3000 nm.

The generation of the supercontinuum in a ESM fiber has the advantage that the generated spectrum is coupled into the fundamental mode only, which therefore is truly single mode. The guidance in the fundamental mode makes it possible to focus the emerging light in a single small spot, which improves the resolution of the scanning which is inversely proportional with the spot size. The guidance of the light in the fundamental mode will also show very low susceptibility to bending losses. Besides, guidance of the light in the fundamental mode shows no susceptibility to external mechanical or acoustic vibrations. This is a significant improvement for laser system where the distinct laser beams are coupled together via coupling optics to superpose in a single spot. Another advantage of the generation of the supercontinuum light in the ESM fiber is the reduced manpower needed for both the installation and maintenance of the coupling optics to ensure a complete overlap of the beams of the distinct laser sources. It is yet another advantage of the use of ESM fibers in the sorting device that lasers with wavelength separations exceeding the transmission bandwidth of step-index fibers, can now be coupled into and guided in the fundamental mode only, improving the spot characteristics.

In a preferred embodiment of the sorting device, according to the invention, the supercontinuum is generated in an optical fiber. This has the advantage that the broadband spectrum of the supercontinuum is generated in the optical fiber, which can be directly coupled out into an optical focusing system or, with low coupling losses, into an optical waveguide system, such as an endlessly single mode fiber. It is yet another advantage that the whole spectrum at the output of the supercontinuum fiber source is automatically superposed and aligned and can be focused into a single spot.

In a preferred embodiment said optical fiber is a photonic crystal fiber (or holey fiber, or micro-structured fiber). This has the advantage that the spectrum of the supercontinuum can be tailored by the design parameters of the holey structure of the cladding. This also has the advantage that the pumping wavelength can be chosen, such that it matches commercially available laser sources.

In a preferred embodiment said photonic crystal fiber is an endlessly single mode fiber. This has the advantage that the generated supercontinuum is coupled in the fundamental mode only over the whole spectral range.

This can for example be done by choosing the lowest zero dispersion point at a higher wavelength, such as 1060 nm, the cut-off wavelength will consequently be shifted to lower wavelengths, such as 300 nm.

In an embodiment said optical fiber is a highly nonlinear fiber (HNLF).

In an embodiment the supercontinuum is generated in the first part of said PCF or HNLF and guided into the sorting system in the second part of the same PCF or HNLF. This has the advantage that no splice with another fiber is needed and the light can be guided into the sorting system in one fiber.

In an embodiment the light of the supercontinuum generated in said optical fiber is coupled directly into an endlessly single mode fiber. This has the advantage that the broad spectrum of wavelengths can be guided in the fundamental mode of the ESMF and allows the light of the spectrum to propagate in a truly single mode regime. Yet another advantage is that if the spectrum, or a part of the spectrum, of the light source is multimode, the light will be guided in the fundamental mode of the ESM fiber only. The Gaussian shape of the fundamental mode has the advantage that the light emerging from the output end of the ESMF can be focused into the smallest possible and most regular spot size. This is advantageous for the sorting device because a smaller spot size increases the sorting resolution and therefore the sorting efficiency, to detect the least possible defects. It is of particular advantage in a sorting device to have a waveguide system, which can guide spatial single mode light in a very broad spectral range resulting in an increase of the number of selection wavelengths.

In an embodiment an ESM fiber is used to guide the light into the sorting device through a system for focusing the light onto the sorting product, where the focusing system can be a stand alone unit or directly attached to the ESM fiber. The use of the ESM fiber to guide light into a focusing system has the advantage that wavelengths, of the entire spectral range of the supercontinuum source, or, which are spectrally widely separated such as in the case of the use of multiple laser source, are guided in the fundamental mode and are single mode. Guidance in the single mode has the advantage that the light can be focused by the focusing system into the smallest possible and most regular spot onto the sorting object.

In another embodiment the object of invention is not only using a supercontinuum light source, but can also include two or multiple lasers coupled into the ESM fiber. This has the advantage that lasers with widely spread wavelengths, i.e. exceeding the transmission bandwidth of a single mode step-index fiber, can be guided in the fundamental mode of the ESM fiber and focused into a single spot where the beams are superposed.

In an embodiment the zero dispersion wavelength of the optical fiber is closely situated to the wavelength of low-cost pump lasers as used in the supercontinuum light source.

In an embodiment a small size low cost pump laser is used. This has the advantage that the total size of the supercontinuum light source can be reduced.

In an embodiment the supercontinuum is generated from the UV to the mid infrared range from 2 to 3 μm. This is of particular relevance for a sorting device, in which sorting parameters have a wavelength in the range of typically in the UV, visible, near infrared and also in the infrared, especially in the wavelength range of 2 to 3 μm. The range between 2 and 3 μm is of specific relevance for the sorting machine, which makes it possible to sort material with typical absorption spectra in this range, such as for example plastics.

In an embodiment the material of the PCF in which the supercontinuum is generated is non-silica, such as chalcogenide such as selenide PCFs ("Chalcogenide optical fibers target mid-IR applications" J. S. Sanghera et al., Laser Focus World, April 2005, p 83f). The advantage of using non-silica material is the lower losses in the mid infrared wavelength range. Therefore non-silica material can make it possible to generate supercontinuum well above 2000 nm and well above 3000 nm.

In an embodiment the width of the band-pass filters can be chosen to regulate the total power incident on the sorting product (entrance filtering) or the detector (detection side filtering). The power incident on the sorting product or detector is directly proportional with the bandwidth of the band-pass of the filter.

In yet another embodiment a multiple wavelength filter is positioned at the output of the supercontinuum source. This has the advantage that the total optical power, which is coupled into the free space area of the sorting device, can be reduced significantly. This is especially advantageous with respect to an improved usability, which is limited by the laser class of the used light source.

In an embodiment the intensity of the supercontinuum is enhanced in specific wavelength ranges. Enhancement of the intensity in these wavelength ranges will improve the signal to noise ratio accordingly. Enhancement of the intensity is of particular relevance for the sorting device because the accordingly improved signal to noise ratio will allow the use of low cost photo detectors in the sorting device.

Other particularities and advantages of the invention will become clear from the following description of a few specific embodiments of the sorting device and method according to the invention; this description is given as an example only and does not restrict the scope of the claimed protection in any way; the reference figures used hereafter refer to the accompanying drawings.

In the different drawings, the same reference figures refer to identical or analogous elements.

The invention relates in general to a sorting device for characterizing products in a stream of products with a radiation source that generates a light beam having a broadband spectrum and means for moving the products through a detection zone.

Figure 1:
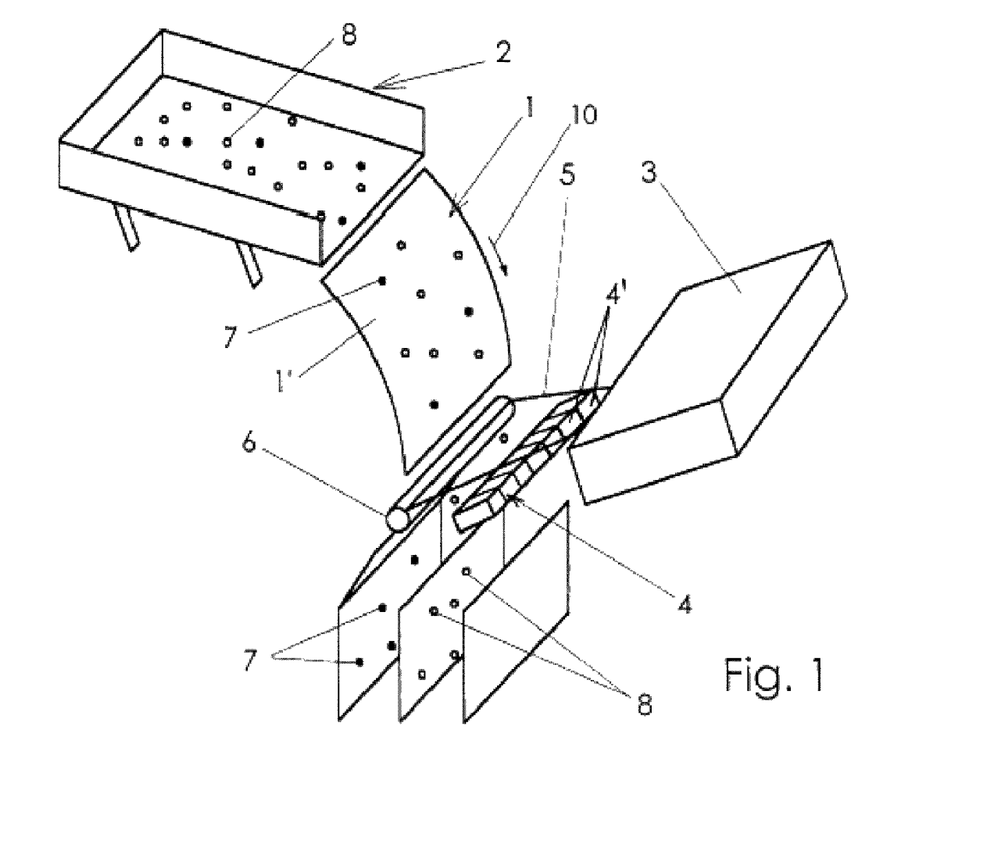
FIG. 1 is a schematic perspective view of a sorting apparatus equipped with a vibrating table, a transport device, an optical system and a removal system, according to the invention.

FIG. 1 is representing such a sorting device with a vibrating table 2 for feeding the products 7 to be sorted to a sloping distribution surface 1 that is generating a stream of products 7 that is moving in free fall through a detection zone 6 situated in front of an optical system 3.

Downstream of the detection zone 6, a removal system 4 comprising a series of pneumatic valves 4', is provided for removing undesired products or foreign objects 8 out of the product stream containing only accepted products 7.

When the products 7 are moving through the detection zone 6, they are impinged by a concentrated light beam 5 of the optical system. This light beam 5 is scanning over the entire width of the detection zone 6.

Figure 2:
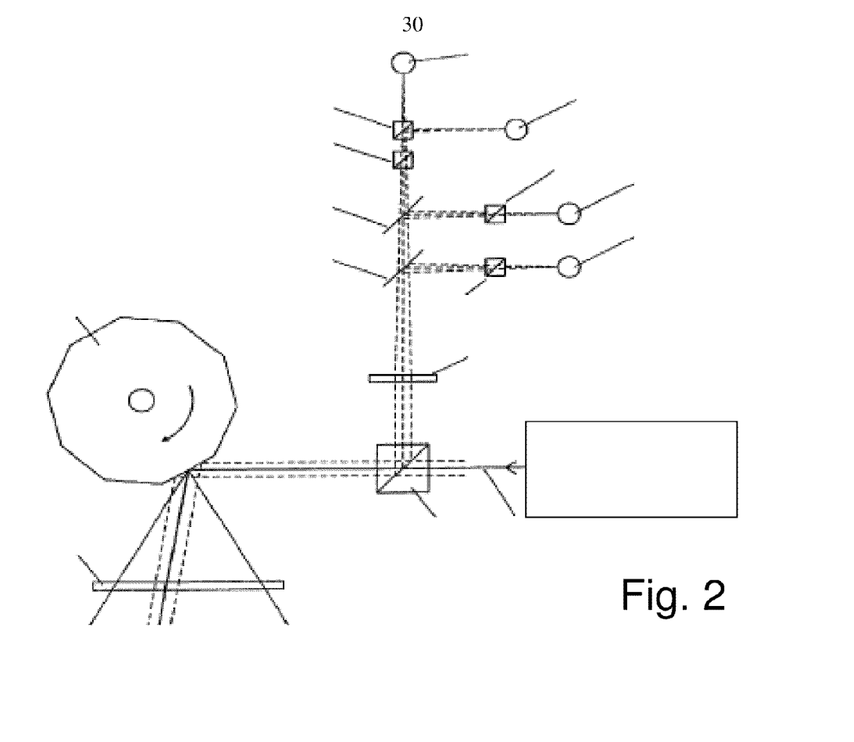
FIG. 2 is a diagrammatic view illustrating the components of an embodiment of the optical system of a sorting apparatus according to the invention.
Figure 3:
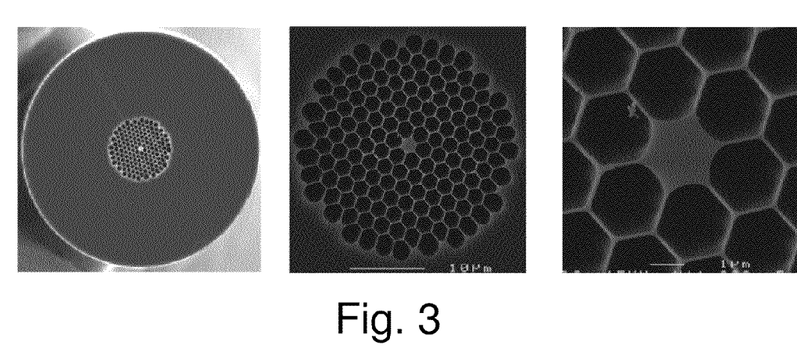
FIG. 3 shows pictures of the cross-section of a typical photonic crystal fiber with a small core for high light confinement and single mode guidance.
Figure 4:
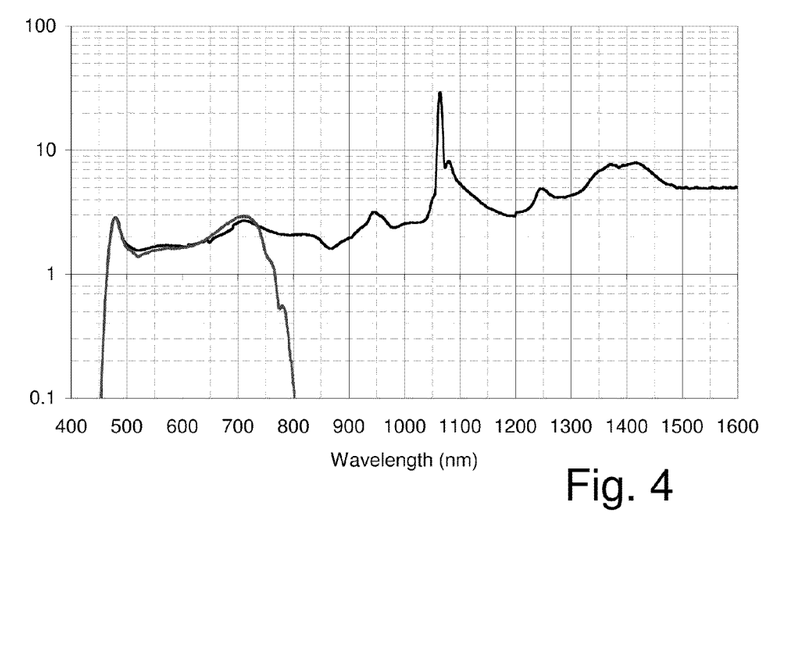
FIG. 4 shows a typical spectrum of a supercontinuum generated in a silica PCF (for example Fianium SC450).
Figure 5:
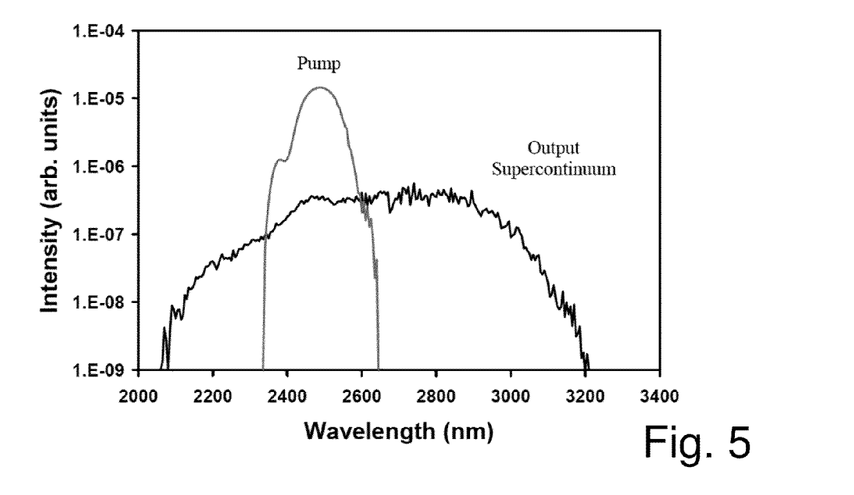
FIG. 5 shows a typical spectrum of a supercontinuum generated in a non-silica PCF, in this case a 1 m sample of an As—Se photonic crystal fiber. Taken from L. B. Shaw et al, "IR supercontinuum generation in As—Se Photonic Crystal Fiber," in Advanced Solid State Photonics., Vol. 98 of OSA Proceedings Series (Optical Society of America, Washington, D.C., 2005), pp. 864-868.
Figure 6:
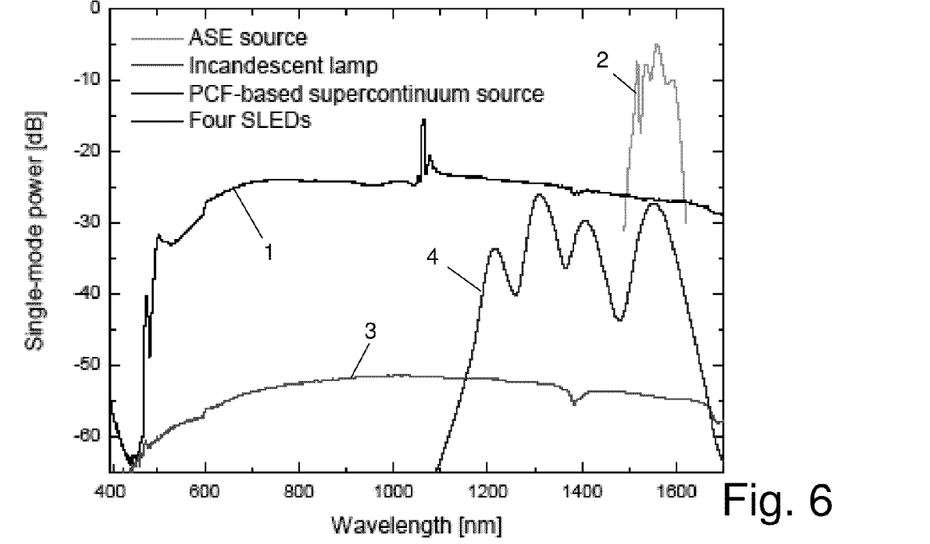
FIG. 6 shows the spectra of four different light sources including 1. the supercontinuum source, 2. an amplified spontaneous emission (ASE) source, 3. an incandescent lamp and 4. multiple super light emitting diodes (SLED) [Taken from Application Note Supercontinuum of the company Crystal Fibre A/S].

The optical system 3 is represented in a diagrammatic way in FIG. 2 and comprises a light source 11 generating said light beam 5, a rotating polygon mirror 12 and a number of optical elements.

Said light beam 5 is directed from the light source 11 through a beam splitter 13 towards the rotating polygon mirror 12 such that the light beam 5 is reflected by this mirror and scans the products 7 moving through the detection zone 6.

The light beam 5 thus impinges upon said products 7 in the detection zone 6 such that light is scattered and/or reflected by the products 7. This scattered and/or reflected light is returned by the rotating polygon mirror 12 towards the beam splitter 13. This beam splitter 13 is, for example, a polarizing beam splitter, and directs the light that is scattered and/or reflected by the products 7 towards a focusing lens 14 and further to detection means comprising detectors 15, 16, 17 and 18.

Said light source 11 comprises a supercontinuum radiation source as already described above and generates, for example, a continuous broadband light with a high spectral density comprised between 300 nm and 3000 nm. This light beam presents highly spatial coherency such that a concentrated light beam is obtained with a cross-sectional diameter that is preferably at least an order of magnitude smaller than the average size of the products to be sorted, and advantageously at least smaller than the defects of the products that have to be detected for sorting purposes.

Further the detection means comprise dichroic mirrors 19 and 20 for directing light with selected wavelengths towards the detectors 15, 16, 17 and 18. These wavelengths are selected in function of the products to be sorted and the defects of the products that are to be detected and are known for a person that is confident with the concerned optical sorting technologies. Some specific embodiments of the detection means are, for example, disclosed in the document U.S. Pat. No. 6,864,970.

According to a preferred embodiment of the sorting device, according to the invention, bandwidth filters are provided between the light source 11 and the detection zone 6. These bandwidth filters are chosen such that they permit the passing of light in a spectral band situated around the different wavelengths that are selected for sorting the products. The width of these spectral bands is chosen such that interference phenomena that would possibly generated at the surface of the products are avoided. By doing so, a very accurate signal is obtained at the detectors 15, 16, 17 and 18.

The bandwidth around said selected wavelengths is preferably of the order of 5 to 30 nm. Excellent results have been obtained with a bandwidth of the order of 10 to 20 nm.

For detecting certain defects or for sorting certain products, sorting is based on fluorescence properties of the products. In these applications of the sorting device, at least a spectral band-block filter is provided in the optical path of said light beam between said supercontinuum radiation source and said detection zone. This spectral band-block filter is substantially preventing that light that is generated by fluorescence through the impingement of light onto said products with a wavelength situated outside the spectral band blocked by this filter, is reaching the detecting means. Preferably, such a band-block filter is positioned between the light source and the location where the impinging light beam is separated from the by the products reflected and/or scattered light, i.e. between the light source and the beam splitter 13.

The sorting apparatus, according to the invention is of particular interest if said bandwidth filters and/or said band-block filters are formed by tunable optical filter, and/or bandwidth-variable tunable filters. In such a case the sorting device becomes very flexible since almost any product can be sorted on basis of any specific selected wavelengths of light.

Figure 7:
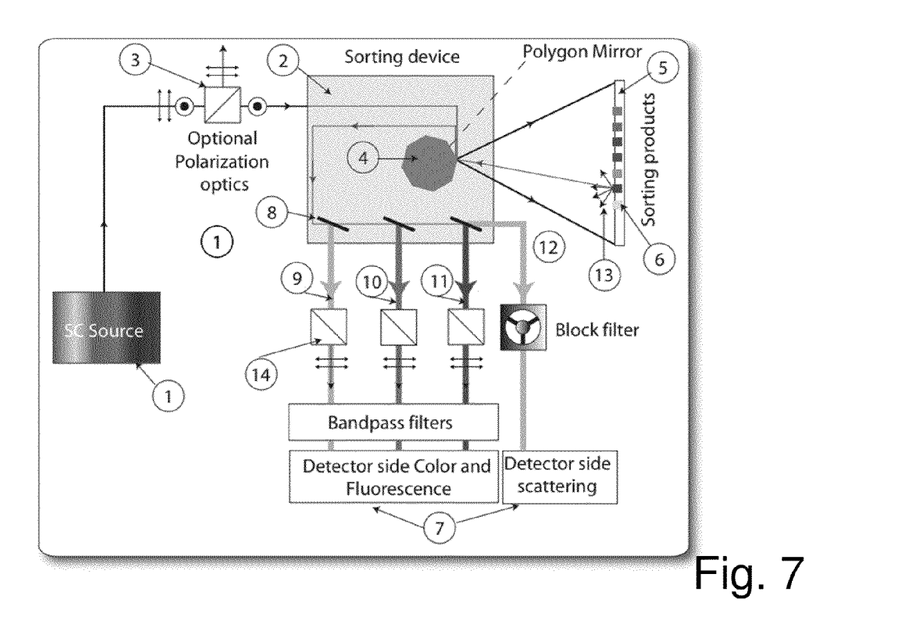
FIG. 7 shows a schematic impression of the sorting device with a supercontinuum light source.

When generating a supercontinuous light beam in a non-linear PCF, a high intensity pulse is guided into the fiber by means of a pump laser. A filter is, preferably placed in order to remove the high intensity component.
FIG. 7

Light emitted by the supercontinuum (SC) source (1) is guided into the sorting device (2). If the output of the supercontinuum source (1) is non-polarized use can be made of broadband polarization optics (3), such as polarization beam splitters to polarize the beam. The light is reflected and spread by a fast rotating polygon mirror (4) over a wide range (5) or scanning line in a detection zone, where the products (6) are to be detected for sorting. The scattered and/or reflected light (13) is a fingerprint for the detected product and is collected by the polygon mirror (4) and guided via a system of lenses and mirrors to the detection side (7). At the detection side the light is split in the spectral components of interest by dichroic mirrors (8). These spectral components could for example be the colors blue (9), green (10) and red (11). Directly reflected light at the products is blocked by the polarization beam splitters (14). An infrared signal can be used for sorting on scatter behavior of the product (12). The detector signals of a blue, red and infrared channel originating from a single supercontinuum source with an endlessly single mode fiber output are shown in FIGS. 11 and 12.

Figure 8:
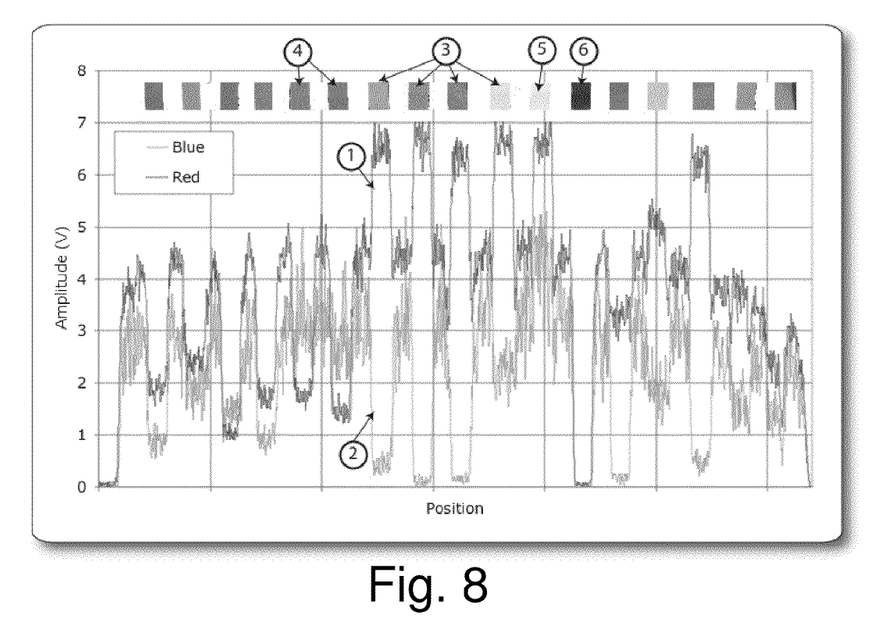
FIG. 8 shows the traces of the detector signals of the sorting device equipped with a supercontinuum light source (Fianium SV450-4).

FIG. 8 shows the traces of the detector signals of the sorting device equipped with a supercontinuum light source (Fianium SV450-4). In this case the red (1) and the blue (2) signals are shown (corresponding with number 11 and 9 respectively in FIG. 7). Shown is the color detection of several samples of distinct color placed at the position of the scanning line (see FIG. 10, number 5). The red samples (3) give a high signal of the red trace (1) while the blue trace (2) should be low. Obviously, the blue samples (4) will result in a high blue and low red detector signal. In the case of a white (5) and a black (6) sample both the corresponding red (1) and blue (2) detector signals will be high and low respectively.

Figure 9:
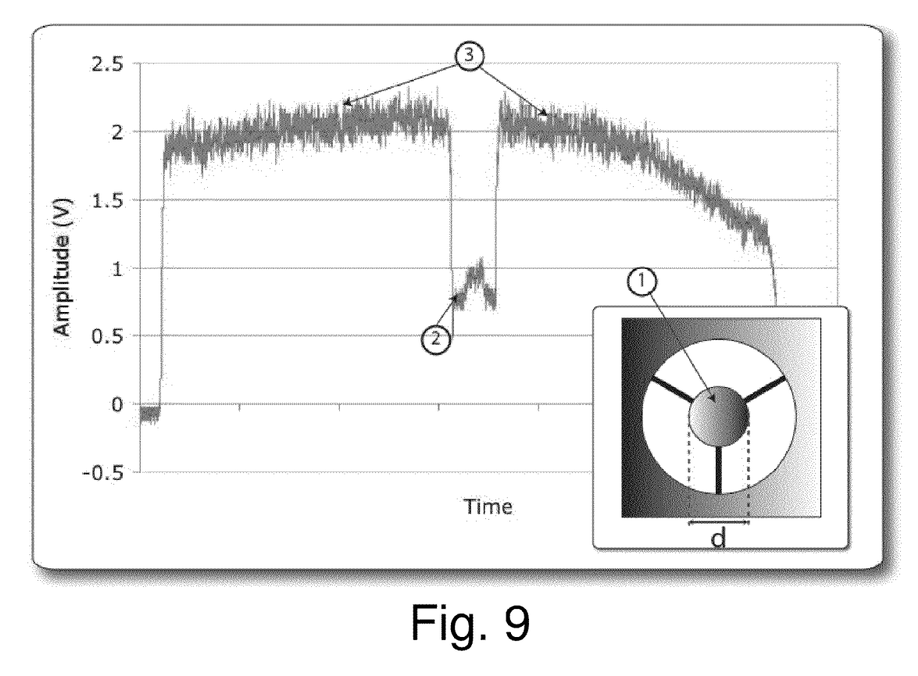
FIG. 9 shows the trace of the infrared detector of the scatter signal (number 12 in FIG. 7).

FIG. 9 shows the trace of the infrared detector of the scatter signal (number 12 in FIG. 7). In front of the detector a metal blocking filter (1) with diameter D is used to reject the signal of the direct reflection at the surface of the sample and only the scattered signal is transmitted. At the scanning line (FIG. 10, number 5) both a white piece of paper is placed (not shown) causing a high reflection and a so called back-drum with a high degree of scattering. Consequently the infrared detector will respond with a low signal at the location of the white paper (2) and a high signal elsewhere (3).

Figure 10:
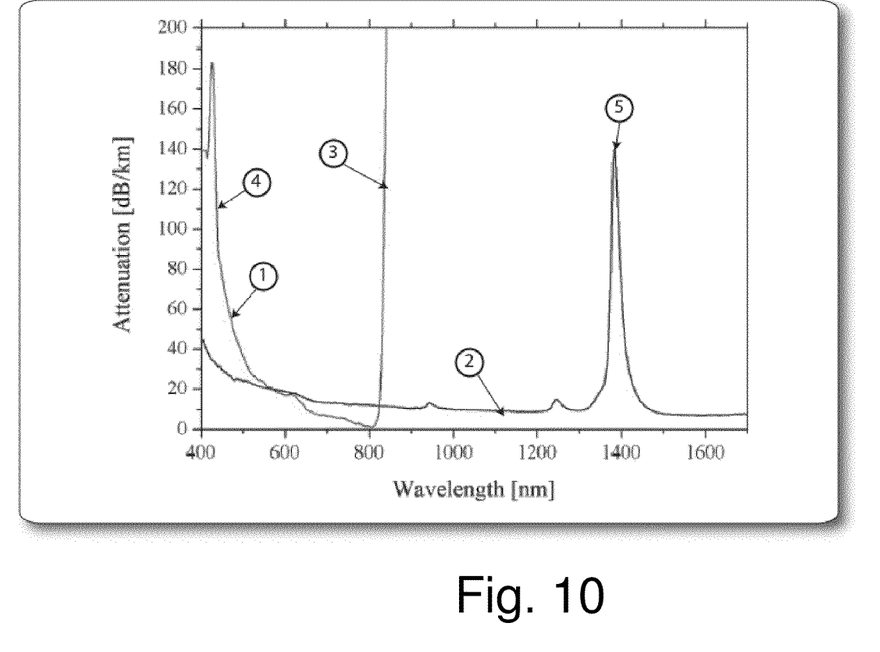
FIG. 10 shows the transmission curves for the fundamental mode in a step-index fiber (1) and an endlessly single mode photonic crystal fiber (2) respectively.

FIG. 10 shows the transmission curves for the fundamental mode in a step-index fiber (1) and an endlessly single mode photonic crystal fiber (2) respectively. The data is taken from M. D. Nielsen, J. R. Folkenberg, N. A. Mortensen, and A. Bjarklev☐ "*Bandwidth comparison of photonic crystal fibers and conventional single-mode fibers*" Optics Express 12, 430 (2004). The spectral bandwidth of the transmission of the fundamental mode in the step-index fiber is clearly bounded by both the high cladding losses and coupling to higher order modes at the high (3) and low (4) wavelength sides respectively. Contrary to the step-index fiber, the endlessly single mode photonic crystal fiber exhibits a no losses to cladding modes at the high wavelength side and shows only coupling to higher order modes below the cut-off wavelength which can be much lower than in a step-index fiber. The high peak at around 1.4 µm originates from a water absorption line, which is dependent on the manufacturing process.

The invention claimed is:

1. Sorting device for characterizing products in a stream of products with a radiation source that generates a spatial coherent light beam having a broadband spectrum and means for moving the products through a detection zone, the device further including a scanning element for scanning the light beam over the width of the detection zone, whereby said light beam impinges upon said products in the detection zone such that light is scattered and/or reflected by the products, and detection means for detecting said scattered and/or reflected light, said detection means cooperating with a processing unit for characterizing the products, wherein said radiation source comprises a supercontinuum radiation source generating a spatial coherent light beam such that a concentrated light beam is obtained.

2. Device according to claim 1, wherein at least a bandwidth filter is provided that permits the passing of a light beam towards the detection means with a bandwidth that is larger than a bandwidth at which interference phenomena are generated at the surface of the products.

3. Device according to claim 1, wherein at least a bandwidth filter is provided that permits the passing of a light beam towards the detection means with a bandwidth that is in between 5 and 30 nm, around a wavelength selected for sorting the products.

4. Device according to claim 1, wherein at least a spectral band-block filter is provided in the optical path of said light beam between said supercontinuum radiation source and said detection zone, whereby the spectral band-block filter is substantially preventing that light that is generated by fluorescence through the impingement of light onto said products with a wavelength situated outside the spectral band blocked by this filter, is reaching the detecting means.

5. Device according to claim 1, wherein said detection means comprise means for filtering selected spectral components.

6. Device according to claim 1, wherein said supercontinuum radiation source comprises a photonic crystal fiber for generating a supercontinuum radiation.

7. Device according to claim 1, wherein said photonic crystal fiber is an endlessly single mode fiber.

8. Device according to claim 1, wherein said light beam is guided by a endlessly single mode fiber from the radiation source towards a focusing system for directing the beam to the detection zone.

9. Device according to claim 1, wherein the scanning element, comprises a rotating polygon mirror.

10. Device according to claim 1, wherein the spectrum of said continuum radiation source comprises light with wavelength between 1100 and 1600 nm.

11. Device according to claim 1, wherein the spectrum of said continuum radiation source comprises light with wavelength between 1000 and 3000 nm.

12. Device according to claim 1, wherein the spectrum of said continuum radiation source comprises light with wavelength between 350 and 3000 nm.

13. Method for inspecting a stream of products in which at least one spatial coherent light beam is directed towards said product stream, comprising moving the products in a particular direction through a detection zone, scanning said light beam is scanning over the width of the detection zone such that said light beam is at least partially scattered and/or reflected by the products, sorting the products on basis of the measured scattered and/or reflected light, and wherein said light beam is generated by a supercontinuum radiation source such that a spatial coherent concentrated light beam is obtained.

14. Method according to claim 13, wherein said light beam is a supercontinuum generated in an optical fiber.

15. Method according to claim 13, wherein only selected spectral components of the scattered and/or reflected light are detected.

16. Method according to claim 15, wherein only selected spectral components of the light beam impinge upon the products in said detection zone.

17. Device according to claim 1, wherein at least a bandwidth filter is provided that permits the passing of a light beam towards the detection means with a bandwidth that is of the order of 10 to 20 nm, around a wavelength selected for sorting the products.

18. Device according to claim 5, wherein said means for filtering selected spectral components are dichroic mirrors.

* * * * *